United States Patent [19]

Yagawara et al.

[11] Patent Number: 5,250,170
[45] Date of Patent: Oct. 5, 1993

[54] GAS SENSOR HAVING METAL-OXIDE SEMICONDUCTOR LAYER

[75] Inventors: Shinji Yagawara; Wasaburo Ohta, both of Yokohama, Japan

[73] Assignee: Ricoh Company, Ltd., Tokyo, Japan

[21] Appl. No.: 668,617

[22] Filed: Mar. 13, 1991

[30] Foreign Application Priority Data

Mar. 15, 1990 [JP] Japan .................. 2-65258
Jun. 8, 1990 [JP] Japan .................. 2-150408
Sep. 10, 1990 [JP] Japan .................. 2-239691

[51] Int. Cl.$^5$ .............................. G01N 27/12
[52] U.S. Cl. ............... 204/431; 73/31.06; 338/34; 422/98
[58] Field of Search .......... 204/425, 424, 431, 432; 338/34, 35; 73/31.06; 422/98

[56] References Cited

U.S. PATENT DOCUMENTS 4,580,439 4/1986 Manaka ........................... 73/23
5,003,812 4/1991 Yagawara et al. ............... 73/31.06

Primary Examiner—John F. Niebling
Assistant Examiner—William T. Leader
Attorney, Agent, or Firm—Oblon, Spivak, McClelland, Maier & Neustadt

[57] ABSTRACT

A gas sensor includes a substrate, a heater member formed on the base member, a gas sensitive structure formed on the heater member by a process comprising the following steps of forming a stacked layer structure on the heater member, the stacked layer structure including at least a metal-oxide semiconductor layer and an insulating film, and carrying out a heat treatment with respect to the stacked layer structure so that a constituent of the insulating film is diffused in spaces among crystal particles of the metal-oxide semiconductor layer, and electrode layers are in contact with the gas sensitive structure.

12 Claims, 4 Drawing Sheets

GAS SENSOR HAVING METAL-OXIDE SEMICONDUCTOR LAYER

BACKGROUND OF THE INVENTION

The present invention generally relates to a gas sensor for detecting a gas in an ambience, and particularly to a gas sensor having a metal-oxide semiconductor layer in which a characteristic thereof can be stable.

Conventionally, the following two types of gas sensors, in each of which a metal-oxide semiconductor is used as a gas sensitive material which can respond to a predetermined gas has been known. In a first type gas sensor, a heater layer is provided via an electrode layer and an insulating layer on a back of the metal-oxide semiconductor layer. In a second type gas sensor, electrodes, and heater coils are provided in a metal-oxide semiconductor block. The gas is absorbed by the metal-oxide semiconductor layer or block, so that a resistance value of the metal-oxide semiconductor layer which is heated by the heater layer or the heater coil is changed. That is, these types of gas sensors detect the gas based on the changing of the resistance value of the metal-oxide semiconductor.

The first type of gas sensor has, for example, a structure as shown in FIGS. 1A and 1B. FIG. 1A is a cross sectional view of the gas sensor, and FIG. 1B is a perspective view thereof.

Referring to FIGS. 1A and 1B, a heater layer 2 is formed on a substrate 1 having an adiabatic characteristic. An insulating layer 3 is formed on the heater layer 2 and electrode layers 41 and 42 are separated from each other and provided on the insulating layer 3. Then a metal-oxide semiconductor layer 51 is formed between the electrode layers 41 and 42 on the insulating layer 3 so that respective side portions of the metal-oxide layer 51 are in contact with the electrode layers 41 and 42, respectively. In a case where the substrate 1 is formed of a conductive material, another insulating layer needs to be provided between the substrate 1 and the heater layer 2. A wire 61 is bonded on an end portion of the heater layer 2 and a wire 62 is bonded on another end portion thereof. Power is supplied via the wires 61 and 62 from a power supply to the heater layer 2. That is, the wires 61 and 62 function as power supplying lines. A wire 71 is bonded on the electrode layer 41 and a wire 72 is bonded on the electrode layer 42. A detecting signal is generated between wires 71 and 72. The wires 71 and 72 function as signal output lines.

FIG. 2 shows another embodiment of the first type gas sensor. In FIG. 2, those parts which are the same as those shown in FIGS. 1A and 1B are given the same reference numbers.

In FIG. 2, the metal-oxide semiconductor layer 51 (a gas sensitive layer) is formed on the insulating layer 3 before the electrode layers 41 and 42 are formed thereon. That is, an edge portion of each of the electrode layers 41 and 42 is provided on a corresponding edge portion of the metal-oxide semiconductor layer 51.

The second type of gas sensor has, for example, a structure as shown in FIG. 3.

Referring to FIG. 3, four electrode pins 8a, 8b, 8c and 8d are provided on a base member 12 having a disc shape so that each of the electrode pins 8 projects from both sides of the base member 12. A gas sensitive material which is a sinter of the metal-oxide semiconductor is mounted on the base member 12. The gas sensitive material 52 has, for example, a 2 or 3 mm cubic shape. First and second heater coils 43 and 44 are laid in the gas sensitive material 52. The first heater coil 43 is connected between the electrode pins 8a and 8b, and the second heater coil 44 is connected between the electrode pins 8c and 8d. A detecting signal is output, for example, between the electrode pin 8b connected to the first heater 43 and the electrode pin 8d connected to the second heater 44.

In the second type of gas sensor described above, the gas sensitive material 52 formed of the metal-oxide semiconductor has a relatively large size, so that power is consumed by the first and second heaters 43 and 44. In addition, the heat capacity of the gas sensitive material 52 is large, so that the response characteristic is poor.

In the first type of gas sensor as shown in FIGS. 1A, 1B and 2, the gas sensitive material has a thin film shape, so that the power consumed by the heater layer 2 is small and the response characteristic is good. However, it is easy for a sensing characteristic, such as sensitivity with respect to the gas, to deteriorate with the passage of time, so that this first type of gas sensor has not been put into practical use yet.

The sensitivity with respect to the gas deteriorates when the size of each crystal particle of the metal-oxide semiconductor increases. The gas sensor is generally used under a condition of 300°–450° C., so that the size of each crystal particle of the metal-oxide semiconductor increases when the gas sensor is being used for a long time. Thus, when the size of each crystal particle of the metal-oxide semiconductor increases, an absorption area in which the gas should be absorbed decreases and the chemical activation of the metal-oxide semiconductor decreases. Therefor, the sensitivity with respect to the gas decreases.

SUMMARY OF THE PRESENT INVENTION

Accordingly, a general object of the present invention is to provide a novel and useful gas sensor in which the disadvantages of the aforementioned prior art are eliminated.

A more specific object of the present invention is to provide a gas sensor in which the sensing characteristic hardly deteriorates with the passage of time.

The above objects of the present invention are achieved by a sensor comprising: a base member including a heater member for generating heat; a gas sensitive structure formed on the base member by a process comprising the following steps (a) and (b) of, (a) forming a stacked layer structure on the base member, the stacked layer structure including at least a metal-oxide semiconductor layer and an insulating film, and (b) carrying out a heat treatment with respect to the stacked layer structure so that a constituent of the insulating film is diffused in spaces among the crystal particles of the metal-oxide semiconductor layer; and electrode layers in contact with the gas sensitive structure.

Additional objects, features and advantages of the present invention will become apparent from the following detailed description when read in conjunction with the accompanying drawings.

DETAILED DESCRIPTION OF THE INVENTION

Figure 1A:
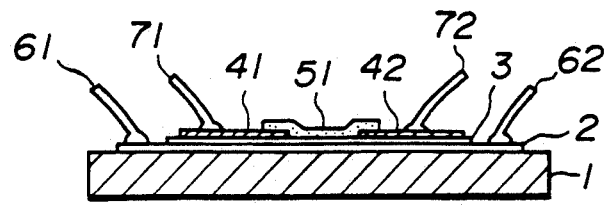
FIG. 1A is a cross sectional view showing a structure of a gas sensor having a thin film gas sensitive layer.
Figure 1B:
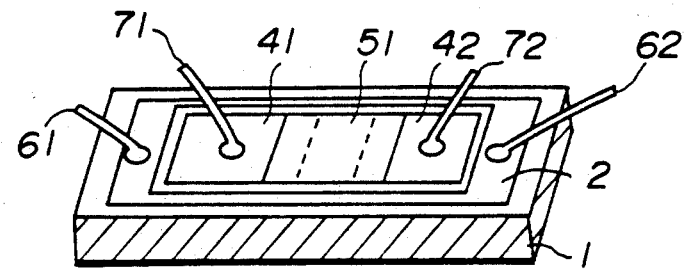
FIG. 1B is a perspective view showing a gas sensor having a thin film gas sensitive layer.
Figure 2:
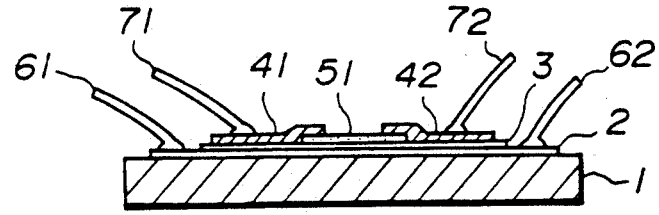
FIG. 2 is a cross sectional view showing another structure of a gas sensor having a thin film gas sensitive layer.
Figure 3:
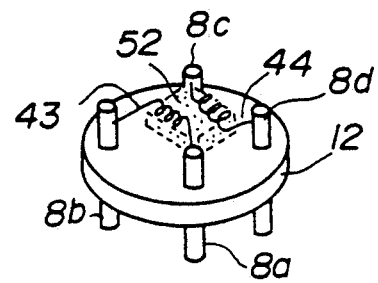
FIG. 3 is a perspective view showing a conventional gas sensor.

A gas sensor which has a thin film metal-oxide semiconductor layer as a gas sensitive material (hereinafter referred to as a thin film type gas sensor) is normally used under a high temperature condition of 300°–450° C., so that a crystallizing process in the metal-oxide semiconductor proceeds when the thin film type gas sensor is used for a long time. Thus, the size of each crystal particle of the metal-oxide semiconductor increases, so that an absorption area in which the gas should be absorbed decreases, a chemical activation of the metal-oxide semiconductor decreases and so on. As a result, sensitivity with respect to the gas deteriorates. In addition, in a case where the thin film type gas sensor is intermittently used, a high temperature (300°–450° C.) and a room temperature (for example, 25° C.) are alternately supplied to the thin film type gas sensor. Thus, as a thermal expansion coefficient of the metal-oxide semiconductor layer differs from that of a substrate or another layer, a pull stress or a compressive stress is generated in the metal-oxide semiconductor layer. Thus, dislocation slips in the metal-oxide semiconductor and a hillock grows therein so that strain based on the above stress is relaxed. When a crystal structure in the metal-oxide semiconductor layer is changed by the slipping of the dislocation and the growth of the hillock, the sensitivity with respect to the gas and the resistance thereof are changed.

If the metal-oxide semiconductor layer has been previously annealed at a high as possible temperature, the above phenomena can be prevented from being generated in the metal-oxide semiconductor. However, in the thin film type gas sensor, when the temperature increases during the annealing process, the strength of the metal-oxide semiconductor layer decreases and it becomes easy for the metal-oxide semiconductor layer to flake from another layer in contact therewith. Thus, it is difficult to heat the thin film type gas sensor at a temperature greater than 700°C.

In the gas sensor which has a sintered metal-oxide semiconductor (hereinafter referred to as a sintered type gas sensor), a binder such as SiO$_2$ or Al$_2$O$_3$ is added in the metal-oxide semiconductor block, it is possible to sinter the metal-oxide semiconductor at a high temperature equal to or greater than 1000° C. Also, a process for adding the binder is simple.

However, in the thin film type gas sensor, it is difficult to uniformly add the binder in the metal-oxide semiconductor layer by use of the same process as in the above sintered type gas sensor.

Thus, a gas sensor according to the present invention has a structure made by the process comprising the steps of depositing an insulating film having a relatively high melting point on the metal-oxide semiconductor layer so that a composite structure thereof is obtained, and carrying out a heat treatment with respect to the composite structure. It has been found that it is hard for the sensing characteristic to deteriorate with the passage of time in the gas sensor having the above structure.

A description will now be given of a gas sensor according to the present invention with reference to FIG. 4.

Figure 4:
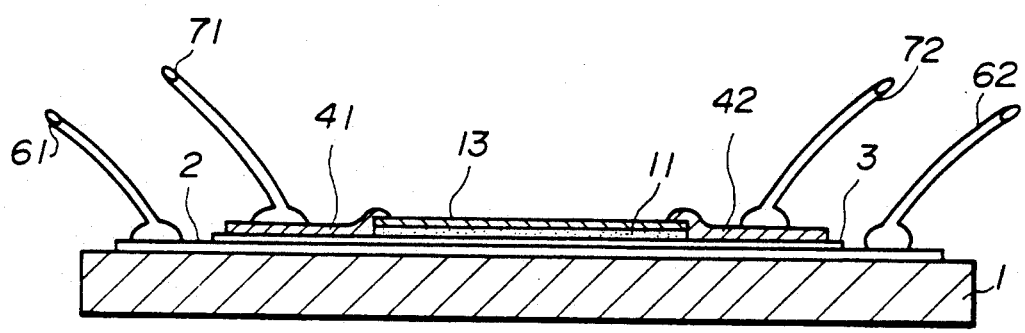
FIG. 4 is a cross sectional view showing a structure of a gas sensor having a thin film gas sensitive layer, according to a first embodiment of the present invention.

Referring to FIG. 4, a substrate 1 is made of heat resisting ceramic. A heater layer 2 made of platinum is formed on the substrate 1 by spattering so as to have a thin film shaped and an insulating layer 3 made of SiO$_2$ is formed on the heater layer 2 by spattering. A metal-oxide semiconductor layer 11 is formed on the insulating layer 3. The metal-oxide semiconductor layer 3 is made of an oxide metal such as tin (Sn), titanium (Ti), indium (In), nickel (Ni), tungsten (W), cadmium (Cd), iron (Fe), zinc (Zn) or the like. An insulating film 13 is formed on the metal-oxide semiconductor layer 11 by vacuum evaporation. The insulating film 13 is made of SiO$_2$, Al$_2$O$_3$, Ta$_2$O$_5$, MgO or the like. It is desirable that the thickness of the metal-oxide semiconductor layer 11 be substantially 500 – 5000 Å and the thickness of the insulating film be substantially 50 – 500 Å. When the thickness of the insulating film 13 is less than 50 Å, it is difficult to prevent the sensing characteristic from deteriorating with the passage of time. When the thickness of the insulating film is greater than 500 Å, it is difficult to obtain enough sensitivity with respect to the gas.

After the insulating film 13 is formed on the metal-oxide semiconductor 11, the stacked layer structure consisting of the substrate 1, the heater layer 2, the insulating layer 3, the metal-oxide semiconductor layer 11 and the insulating film 13 is annealed at a predetermined temperature for a predetermined time. When the annealing process is completed, electrode layers 41 and 42 are formed on the insulating layer 3 by spattering so that each of the electrode layers 41 and 42 is connected to a corresponding side of a structure obtained by the annealing of metal-oxide semiconductor layer 11 and the insulating film 13. The electrodes layer 41 and 42 can also be formed on the insulating layer 3 before the annealing process is carried out.

It has been found that the gas sensor made as described above has a sensitivity with respect to the gas which hardly deteriorates with the passage of time.

Figure 6:
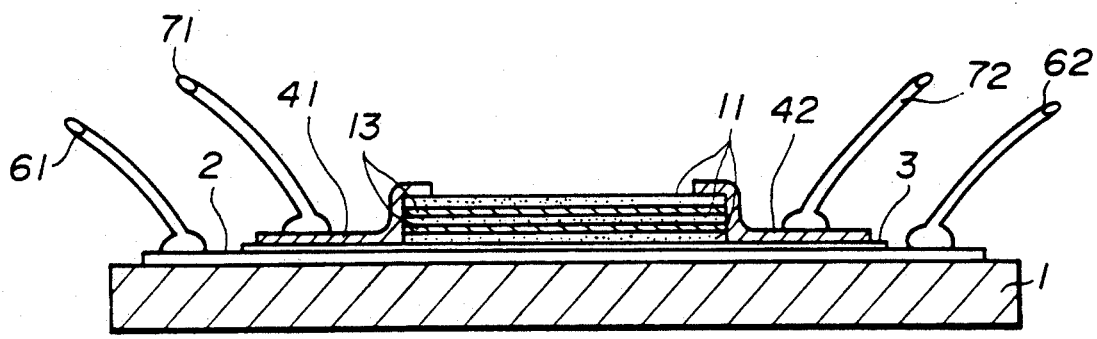
FIG. 6 is a cross sectional view showing a structure of a gas sensor having a thin film gas sensitive layer, according to a second embodiment of the present invention.

A description will now be given of another gas sensor according to the present invention with reference to FIG. 6. In FIG. 6, those parts which are the same as those shown in FIG. 4 are given the same reference numbers.

Referring to FIG. 6, a plurality of metal-oxide semiconductor layers 11 and a plurality of insulating films 13 are alternately stacked on the insulating layer 3. After a stacked layer structure consisting of the metal-oxide semiconductor layers 11 and the insulating films 13 are formed, the annealing process is carried out. Then, the electrode layers 41 and 42 are formed on the insulating layer 3 so as to be in contact with the stacked layer structure consisting of the metal-oxide semiconductor layers 11 and the insulating layers 13. It is desirable that the thickness of each metal-oxide semiconductor layer 11 be 500–5000 Å and the thickness of the insulating film 13 be 100–1000 Å. In addition, it is desirable that the number of the metal-oxide semiconductor layers 11 be 2–5 and the number of the insulating films 13 be 1–4.

In each of the structures shown in FIGS. 4 and 6, the wires 61 and 62 for supplying power to the heater layer 2 are bonded on the heater layer 2, and the wires 71 and 72 for outputting the detecting signal are bonded on the electrode layers 41 and 42. In addition, the metal-oxide semiconductor layer 11 can be formed by vacuum evaporation, spattering or the like. It is desirable that the metal-oxide semiconductor layer 11 be formed by a "Thin Film Evaporation Apparatus" disclosed in Japanese Patent Laid Open Publication No. 59-89763. Ohta, who is one of the inventors of the present invention, is also the inventor of this apparatus.

The present invention can also be applied to a gas detecting film in a gas sensor having a micro heater structure disclosed in Japanese Patent Laid Open Publication No.1-167645, which has been proposed by the inventors of the present invention.

EXAMPLES

EXAMPLE 1

A gas sensor had a structure as shown in FIG. 4. In this gas sensor, a tin oxide film was formed as the metal-oxide semiconductor layer 11, and a $SiO_2$ film was formed as the insulating film 13.

The tin oxide film was formed as follows.

Metal tin (Sn) was used as the material which should be evaporated. A vacuum tank is previously maintained at a predetermined pressure in the order of $10^{-4}$Pa, and then oxygen gas was brought into the vacuum tank so that the pressure in the vacuum tank was controlled at 0.2 Pa. Under this condition, a current of 70A was supplied to a filament so that electrons were generated from the filament, and then a voltage of about 100 V was supplied to a grid so that plasma was generated. Thus, the tin oxide film grew at a speed of about 20Å/sec., so that a tin oxide film of 3000Å is formed.

$SiO_2$ was formed on the Tin oxide film as follows.

Oxygen gas was brought into the vacuum tank so that the pressure in the vacuum tank was controlled at 0.1 Pa. Under this condition, SiO was evaporated by a resistor heating process so that a $SiO_2$ film of 100Å was formed on the tin oxide film.

After a stacked layer structure consisting of the tin oxide film and the $SiO_2$ film were formed, the thin film type gas sensor having the stacked layer structure was annealed for 3 hours in oxygen gas at 1000° C.

Even if the tin oxide film was maintained at 1000° C., the tin oxide film formed in accordance with the above process was firm so it did not flake from a layer on which the tin oxide film was formed. In addition, the sensitivity with respect to the gas was high enough. When the gas sensor having the above structure is used at 450° C. for 300 days, the sensitivity with respect to the gas does not deteriorate at all.

Based on the result of Example 1, the inventors of the present invention believe as follows.

Figure 5:
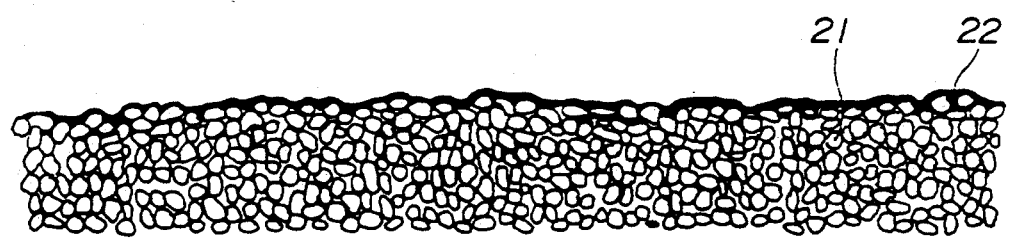
FIG. 5 shows a structure having a metal-oxide semiconductor layer and an SiO$_2$ layer after an annealing process.

Tin oxide is finely crystallized by the annealing process, and then, as shown in FIG. 5, $SiO_2$ 22 is diffused in spaces among crystal particles 21 of tin oxide. The $SiO_2$ 22 diffused in the spaces among the crystal particles 21 functions as a binder so that the tin oxide film becomes firm and the size of each of the crystal particles 21 is prevented from increasing.

Example 2

A gas sensor had a structure as shown in FIG. 6. In this gas sensor, a tin oxide film was formed as the metal-oxide semiconductor layer 11, and a $SiO_2$ film was formed as the insulating film 13.

The tin oxide film is formed as follows.

Metal tin (Sn) was used as a material which should be evaporated. A vacuum tank was previously maintained at a predetermined pressure in the order of $10^{-4}$Pa, and then oxygen gas was brought into the vacuum tank so that the pressure in the vacuum tank was controlled at 0.2 Pa. Under this condition, a current of 70Å was supplied to a filament so that electrons were generated from the filament, and then a voltage of about 100 V was supplied to a grid so that plasma was generated. Thus, the tin oxide film grew at a speed of about 20Å/sec., so that the tin oxide film of 3000Å was formed.

$SiO_2$ was formed on the Tin oxide film as follows.

Oxygen gas was brought into the vacuum tank so that the pressure in the vacuum tank was controlled at 0.1 Pa. Under this condition, SiO was evaporated by a resistor heating process so that a $SiO_2$ film of 100A was formed on the tin oxide film.

The tin oxide films and the $SiO_2$ films, which are formed in accordance with the above processes, are alternately stacked. There are three tin oxide films and each tin oxide film has a 1000 Å thickness. There are two $SiO_2$ is two and each $SiO_2$ film has a 100 Å thickness.

After a stacked layer structure consisting of the tin oxide films and the $SiO_2$ films is formed, the thin film type gas sensor having the stacked layer structure is annealed for 3 hours in oxygen gas at 1000° C.

Even if the oxide films are maintained at 1000° C., each tin oxide film formed in accordance with the above process is firm so as not to flake from a layer on which each tin oxide film is formed. In addition, the sensitivity with respect to the gas is also sufficiently high. When the gas sensor having the above structure is used at 450° C. for 300 days, the sensitivity with respect to the gas does not deteriorate at all.

In this case, also, based on the result of Example 2, the inventors of the present invention believe as follows.

Figure 7:
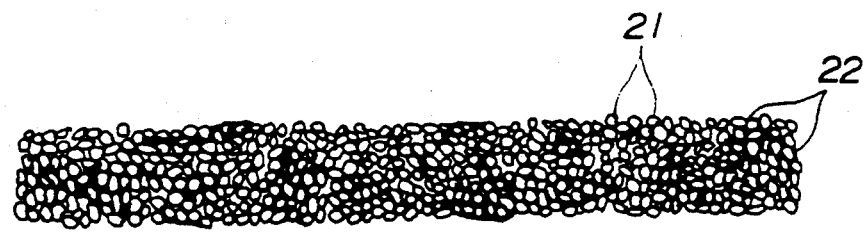
FIG. 7 shows a structure having a metal-oxide semiconductor layer after an annealing process for annealing.

Tin oxide is finely crystallized by the annealing process, and then, as shown in FIG. 7, $SiO_2$ 22 is diffused in spaces among the crystal particles 21 of tin oxide. The $SiO_2$ 22 diffused in the spaces among the crystal particles 21 functions as a binder so that the tin oxide film becomes firm and the size of each crystal particle 21 is prevented from increasing.

Figure 8:
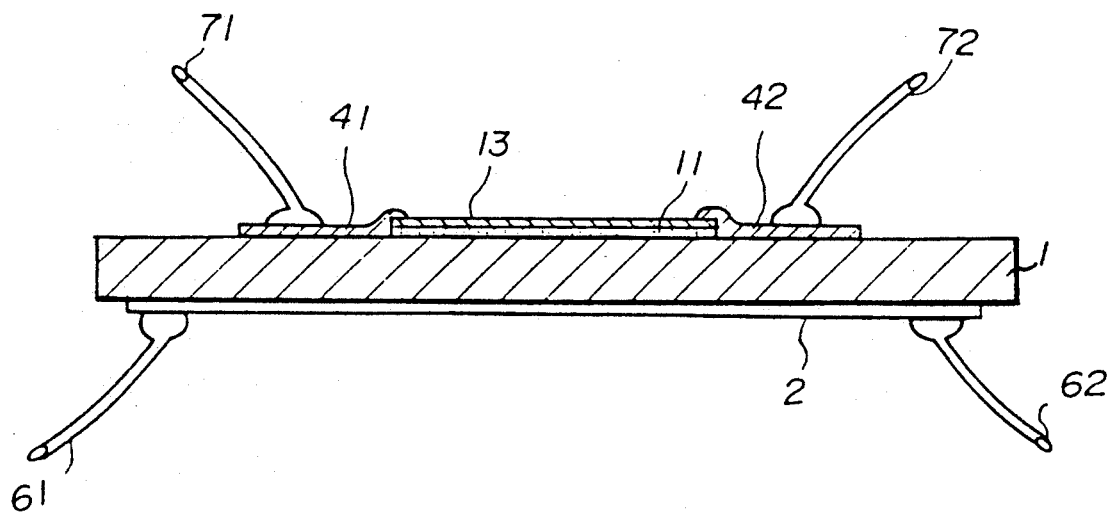
FIG. 8 is a cross sectional view showing another structure of a gas sensor.

The heater layer 2 can be provided on a surface of the substrate 1, opposite to the surface on which the metal-oxide semiconductor layer 51 is provided, as shown in FIG. 8.

The present invention is not limited to the aforementioned embodiments, and variations and modifications may be made without departing from the scope of the claimed invention.

What is claimed is:

1. A gas sensor comprising:

a base member including a heater member for generating heat;

a metal-oxide semiconductor layer in which a resistance thereof is changed by a gas which is in contact with said metal-oxide semiconductor layer, said metal-oxide semiconductor layer being formed on said base member;

an insulating thin film stacked on said metal-oxide semiconductor layer so as to cover a whole surface of said metal-oxide semiconductor layer; and electrodes, in contact with said metal-oxide semiconductor layer, for detecting a change in the resistance of said metal-oxide semiconductor layer, wherein said metal-oxide layer has a portion in which a material of said insulating thin film fills up spaces among crystals of said metal-oxide semiconductor layer.

2. A gas sensor as claimed in claim 1, wherein said metal-oxide semiconductor layer has a thickness falling into a range of 500 A-5000 A.

3. A gas sensor as claimed in claim 1, wherein said insulating thin film has a thickness falling into a range of 50 A-500 A.

4. A gas sensor as claimed in claim 1, wherein said metal-oxide semiconductor layer is made of oxide of one material selected from the group consisting of tin, titanium, indium, nickel, tungsten, cadmium, iron, and zinc.

5. A gas sensor as claimed in claim 1, wherein said insulating thin film is made of one material selected from the group consisting of $SiO_2$, $Al_2O_3$, $Ta_2O_5$, and Mgo.

6. A gas sensor as claimed in claim 1, wherein said heater member has a heater layer which generates heat when power is supplied from an external power supply to said heater layer and an insulating layer formed on said heater layer.

7. A gas sensor comprising:

a base member including a heater member for generating heat;

a stacked layer structure formed on said base member, said stacked layer structure comprising;

a plurality of metal-oxide semiconductor layers in which a resistance thereof is changed by a gas which is in contact with said metal-oxide semiconductor layers; and one or a plurality of insulating thin films, said metal-oxide semiconductor layers and said one or a plurality of insulating thin films being alternately stacked; and electrodes, which are in contact with said metal-oxide semiconductor layers, for detecting a change in the resistance of said metal-oxide semiconductor layers, wherein each of said metal-oxide semiconductor layers has a portion in which a material of each of said insulating thin films fills up spaces among crystals of each of said metal-oxide semiconductor layers.

8. A gas sensor as claimed in claim 7, wherein each of said metal-oxide semiconductor layers has a thickness falling into a range of 55 A-5000 A.

9. A gas sensor as claimed in claim 7, wherein each of said insulating thin films has a thickness falling into a range of 100 A-1000 A.

10. A gas sensor as claimed in claim 7, wherein each of said metal-oxide semiconductor layer is made of oxide of one material selected from the group consisting of tin, titanium, indium, nickel, tungsten, cadmium, iron, and zinc.

11. A gas sensor as claimed in claim 7, wherein each of said insulting thin films is made of one material selected from the group consisting of $SiO_2$, $Al_2O_3$, $Ta_2OI_5$, and MgO.

12. A gas sensor as claimed in claim 7, wherein said heater member has a heater layer which generates heat when power is supplied from an external power supply to said heater layer and an insulating layer formed on said heater layer.

* * * * *